United States Patent
Faure

(10) Patent No.: US 10,398,526 B2
(45) Date of Patent: Sep. 3, 2019

(54) ASSEMBLY FOR POSITIONING ELECTRODES FOR RADIOFREQUENCY TISSUE ABLATION

(71) Applicant: Trod Medical, Paris (FR)

(72) Inventor: André S. Faure, Palmetto, FL (US)

(73) Assignee: TROD MEDICAL, Paris (FR)

( * ) Notice: Subject to any disclaimer, the term of this patent is extended or adjusted under 35 U.S.C. 154(b) by 688 days.

(21) Appl. No.: 14/954,275

(22) Filed: Nov. 30, 2015

(65) Prior Publication Data
US 2017/0151033 A1    Jun. 1, 2017

(51) Int. Cl.
| | |
|---|---|
| *A61B 90/11* | (2016.01) |
| *A61B 17/34* | (2006.01) |
| *A61B 18/14* | (2006.01) |
| *A61B 18/00* | (2006.01) |
| *A61B 18/12* | (2006.01) |
| *A61B 17/00* | (2006.01) |
| *A61B 90/00* | (2016.01) |

(52) U.S. Cl.
CPC .......... *A61B 90/11* (2016.02); *A61B 17/3403* (2013.01); *A61B 18/1477* (2013.01); *A61B 2017/00274* (2013.01); *A61B 2017/3413* (2013.01); *A61B 2018/00494* (2013.01); *A61B 2018/00529* (2013.01); *A61B 2018/00547* (2013.01); *A61B 2018/00577* (2013.01); *A61B 2018/126* (2013.01); *A61B 2018/1435* (2013.01); *A61B 2090/378* (2016.02)

(58) Field of Classification Search
CPC .................. A61B 17/3403; A61B 2017/00274
See application file for complete search history.

(56) References Cited

U.S. PATENT DOCUMENTS

| | | |
|---|---|---|
| 5,957,935 A | 9/1999 | Brown et al. |
| 6,398,711 B1 | 6/2002 | Green et al. |
| 6,415,679 B1 | 7/2002 | Chiodo |

(Continued)

FOREIGN PATENT DOCUMENTS

WO    WO 2009/138510 A1    11/2009

*Primary Examiner* — Julie A Szpira
(74) *Attorney, Agent, or Firm* — Brian S. Boyer; Syndicated Law, PC

(57) ABSTRACT

Assembly (10) for positioning an electrode assembly (16) for radiofrequency ablation, comprising a first linear motion guide (11) defining a first axis of motion (103) and comprising a first carriage (111) operable to move along the first axis of motion (103), an XY positioner (12) operable to move a second carriage (123) in a two-dimensional space defined by a second axis of motion (104) and a third axis (105) orthogonal to the second axis of motion. The XY positioner is positioned relative to the first linear motion guide (11) such that the second axis of motion and the third axis are orthogonal to the first axis of motion (103). A first coupling means (125, 14) couples the electrode assembly (16) to the second carriage (123). A second linear motion guide (13) defining a fourth axis of motion (106) is disposed such that the fourth axis of motion is parallel to the second axis of motion (104). The second linear motion guide (13) comprises a third carriage (131) operable to move independently of the second carriage (123). A second coupling means (133, 15) for coupling a tissue stabilizing instrument is mounted to the third carriage (131).

13 Claims, 7 Drawing Sheets

(56) References Cited

U.S. PATENT DOCUMENTS

| | | | |
|---|---|---|---|
| 2009/0030339 A1* | 1/2009 | Cheng | A61B 8/0833 600/562 |
| 2010/0036245 A1* | 2/2010 | Yu | A61N 5/1027 600/439 |
| 2011/0071380 A1 | 3/2011 | Goldenberg et al. | |
| 2011/0288541 A1 | 11/2011 | Faure | |

* cited by examiner

ASSEMBLY FOR POSITIONING ELECTRODES FOR RADIOFREQUENCY TISSUE ABLATION

The present invention is related to assemblies for positioning electrodes for radiofrequency tissue ablation and related methods for positioning such electrodes.

US 2011/0288541 (FAURE) 24.11.2011 describes a method of percutaneous treatment of prostate lesions using radiofrequency. The method uses an electrode assembly comprising an outer helical electrode adapted for engaging tissue and an inner electrode, which can be either a straight needle or helical as well, arranged concentric with the outer helical electrode. The outer helical electrode and the inner electrode form a bipolar electrode pair. Both electrodes are positioned relative to the tissue with the aid of an electrode guide and relative to which the electrodes can be advanced or retracted by a screwing movement for the helical electrode and a sliding movement for the straight needle.

The electrode guide is fixed on an XY positioning mount, which in turn is fixed on a linear stepper holding a transrectal ultrasound probe (TRUS), with the axis of the linear stepper being parallel to the axis of the electrodes.

A somewhat similar assembly for positioning straight needles for use in focal ablation or brachytherapy is described in US 2011/0071380 (GOLDENBERG et al.) 24.03.2011. This assembly uses a portal like frame equipped with two linear motion joints adapted for moving a holder for a medical instrument in XY. The holder is additionally equipped with two rotational joints.

Positioning assemblies of the above kind allow for imaging the tissue to be treated simultaneously with the electrode assembly/medical instrument, such that real-time feedback is obtained regarding a correct position of the electrodes/needle. It has however been observed that the tissue to be treated, such as the prostate, may move between the instant of positioning the medical instrument outside the patient and the instant at which the medical instrument engages the tissue. In such cases it may happen that the medical instrument must be retracted, repositioned and inserted again. There is a need in the art of reducing such corrective actions.

It is therefore an object of the present invention to provide electrode positioning assemblies allowing for a more accurate tissue engagement, and possibly with fewer iterations.

According to a general aspect of the invention, there is therefore provided an assembly for positioning electrodes for radiofrequency ablation as set out in the appended claims. Assemblies comprise a first linear motion guide defining a first axis of motion. The first linear motion guide comprises a first carriage operable to move along the first axis of motion. Assemblies can further comprise a connector adapted for attaching an imaging device, such as a transrectal ultrasound probe, to the first carriage. Assemblies can further comprise an XY positioner operable to move a second carriage in a two-dimensional space defined by a second axis of motion and a third axis perpendicular to the second axis of motion. The XY positioner is advantageously positioned relative to the first linear motion guide such that the second axis of motion and the third axis are perpendicular to the first axis of motion. Assemblies can further comprise a first coupling device or means for coupling the electrode assembly to the second carriage.

According to a first aspect, assemblies for positioning the electrode assembly for radiofrequency ablation comprise a second linear motion guide defining a fourth axis of motion. The second linear motion guide is disposed such that the fourth axis of motion is parallel to the second axis of motion. The second linear motion guide advantageously comprises a third carriage operable to move independently of the second carriage. A second coupling device is advantageously mounted to the third carriage for coupling a tissue stabilising instrument thereto.

Since the third carriage moves independently of the second carriage, the positioning of tissue stabilising instruments and radiofrequency electrodes are decoupled. As a result, the radiofrequency electrodes can be repositioned in case of untolerable deviation without affecting tissue stabilisation and the efficiency of the surgical procedure is increased.

According to a second aspect, which can be provided in combination with the first aspect or independently thereof, assemblies for positioning the electrode assembly for radiofrequency ablation comprise a third linear motion guide defining a fifth axis of motion parallel to the first axis of motion. The third linear motion guide is operable to move the first coupling device along the fifth axis of motion.

Since the first coupling device can be adjusted along a direction of insertion of the radiofrequency electrodes (parallel to the first axis of motion), full control of an engagement direction of a helical electrode tip into a tissue or organ to treat can be achieved.

According to a third aspect, which can be provided in combination with either one of or both the first aspect and the second aspect, or independently of both, assemblies for positioning the electrode assembly for radiofrequency ablation comprise a ruler or other suitable member arranged for indicating a position of the second carriage along one of a group consisting of the second axis of motion, the third axis, and as the case may be, the fifth axis of motion, relative to a reference. A device or means for coupling the ruler to a corresponding one of the XY positioner and the third linear motion guide is provided, such as e.g. a set screw or a clamp, wherein the device for coupling is adapted for fixing the ruler at different positions along the corresponding axis, the different positions representative of different ones of the reference.

By changing a position of the ruler, a reference position for the corresponding guide can be changed. By so doing, the rulers can be repositioned to correspond to a coordinate system of the medical imaging device attached to the first linear motion guide. This helps the surgeon to easily and faultlessly read coordinates directly based on the rulers without requiring conversion between coordinate systems.

Related methods for positioning electrode assemblies for radiofrequency ablation are described as well.

Aspects of the invention will now be described in more detail with reference to the appended drawings, wherein same reference numerals illustrate same features and wherein.

Figure 1:
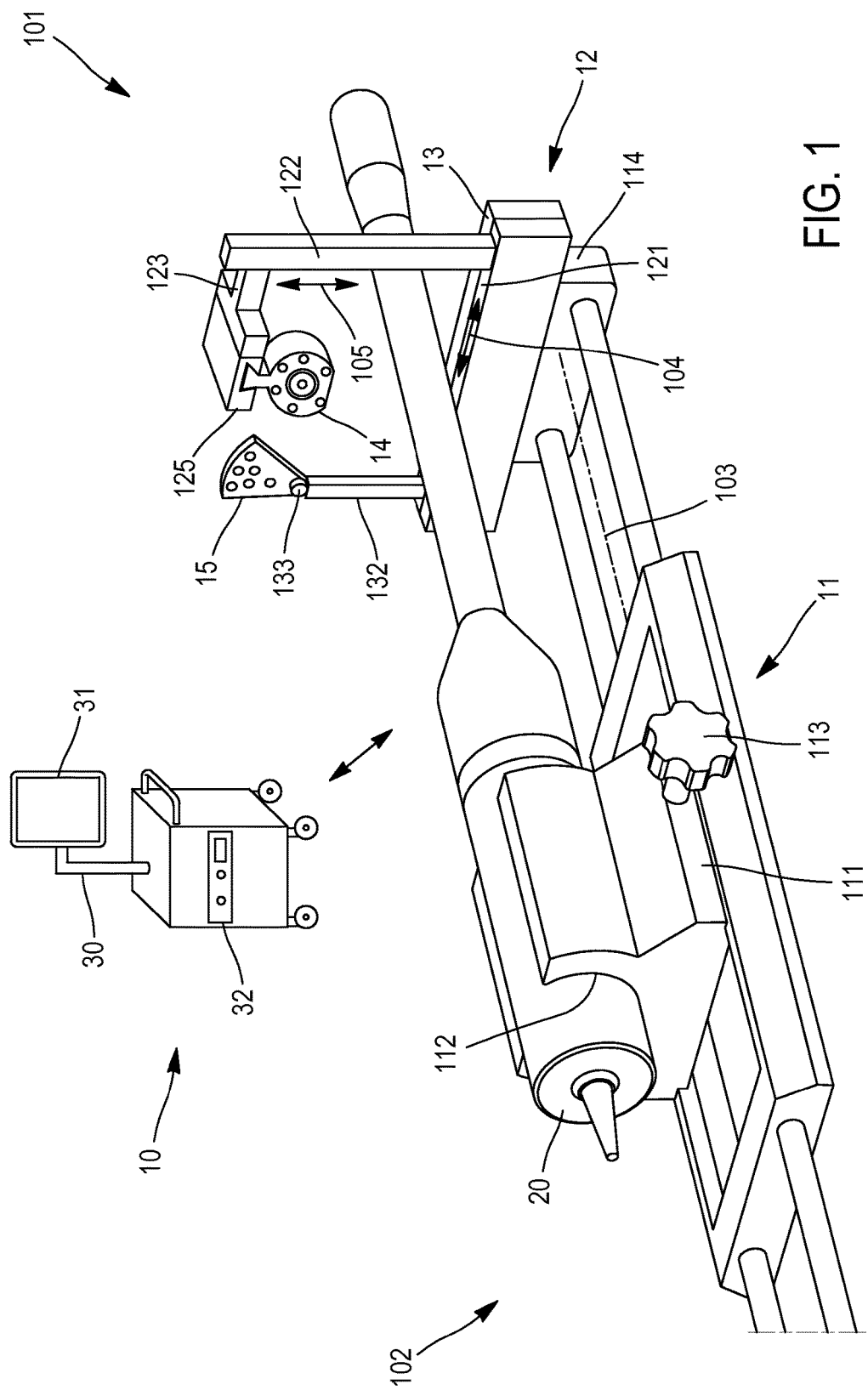
FIG. 1 represents a perspective view of an assembly according to aspects of the invention.

Referring to FIG. 1, there is depicted an assembly 10 for positioning electrodes for radiofrequency ablation according to aspects of the invention. The assembly represented in FIG. 1 is particularly adapted for percutaneous ablation of prostate lesions. It will be convenient to note that the invention is not limited to this particular kind of application and can be used for treating other organs by straightforward adaptation.

The assembly 10 comprises a first linear motion guide 11 oriented to provide motion along a longitudinal axis 103. Longitudinal axis 103 is oriented in a direction from a proximal end 102 towards a distal end 101, wherein the distal end 101 denotes a direction towards the tissue to treat (not shown). In use, longitudinal axis 103 may be directed perpendicular to a surface of the patient's skin. A carriage 111 is adapted for moving along the guide 11, along the direction of axis 103. The carriage 111 may be driven manually, such as through control knob 113, in order to position carriage 111 at a desired location along axis 103. Alternatively, actuators, such as a stepper or servomotor (not shown) may be provided for driving the carriage 111 on the guide 11.

The carriage 111 is provided with a connector 112 for holding an ultrasound imaging device, such as a transrectal ultrasound (TRUS) probe 20 in the instant application. As a result, the ultrasound probe 20 is secured such that it moves integrally with carriage 111. The connector 112 is advantageously mounted on the carriage 111 in such a way that the probe 20 is oriented along the longitudinal axis 103.

Figure 2:
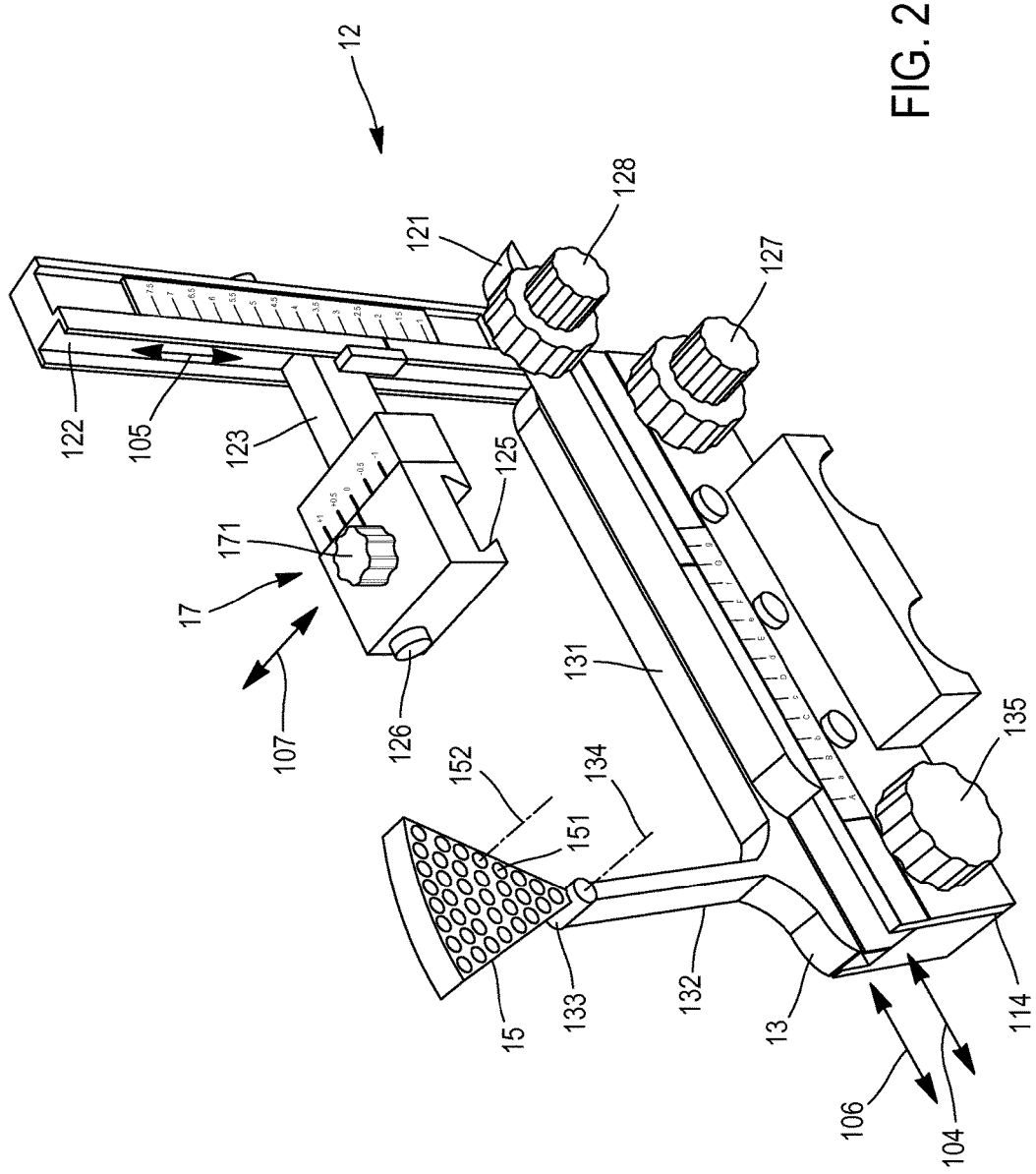
FIG. 2 represents a more detailed perspective view of the XY positioner and additional guides as shown in FIG. 1.

The assembly 10 further comprises an XY positioner 12 which is shown in FIG. 1 mounted to form part of the assembly 10, and which is shown isolated from the longitudinal guide 11 in FIG. 2. The XY positioner 12 is advantageously composed of a first linear motion guide 121 and a second linear motion guide 122 which are arranged in mutually orthogonal directions. The linear motion guide 121 is arranged to provide motion along an axis 104, which is transverse to and advantageously orthogonal to longitudinal axis 103. By way of example, axis 104 may be oriented in a left-right (vertical) direction relative to the ultrasound probe 20, and which may be a direction tangential to the skin surface. The second linear motion guide 122 is arranged to provide motion along an axis 105, which is also transverse to and advantageously orthogonal to longitudinal axis 103. By way of example, axis 105 may be oriented in an up-down (vertical) direction relative to the ultrasound probe 20. The XY positioner 12 further comprises a carriage 123 which is operable to move along the axes 104 and 105 defined by guides 121 and 122. As transverse axes 104 and 105 are mutually orthogonal, it results that the carriage 123 will move in a plane defined by axes 104 and 105.

Figure 3:
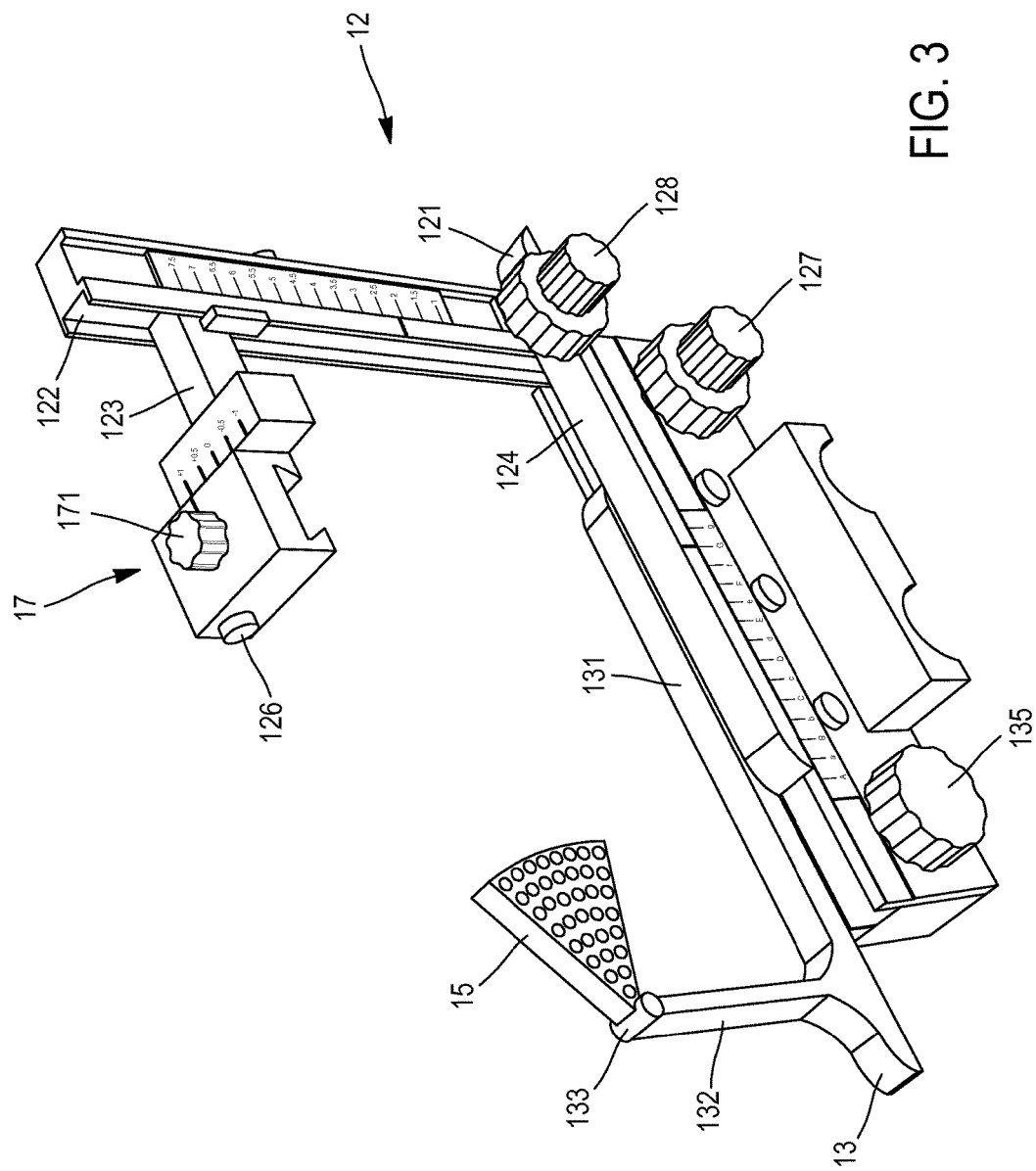
FIG. 3 represents the positioner of FIG. 2 with the horizontal guides arranged in a shifted position.

There are different ways for combining guides 121 and 122 into an XY positioner and any one of these will do. One possibility as shown in FIGS. 1-3 fixes guide 122 to move integrally along guide 121. The guide 122 is fixed on a carriage 124 which is operable to move along guide 121. In this case carriage 123 will be mounted directly on guide 122. Alternatively, guide 121 may be fixed to move integrally along guide 122, in which case carriage 123 would be mounted directly on guide 121. Portal structures, such as described in US 2011/0071380 can be contemplated as well.

The various guides 121 and 122 of the XY positioner can be operated manually, such as through control knobs 127 and 128 respectively. These control knobs may provide separate knobs for coarse and precise positioning. Alternatively, either one or both guides may be provided with suitable actuators providing automatic motion along axes 104 and 105 based on treatment planning control.

The XY positioner 12 may be fixed to a frame 114 which in use is at a fixed position relative to the longitudinal guide 11, as represented in FIG. 1. Frame 114 advantageously comprises fixture means (not shown) for fixing to an external stand, such as to an operating table. In this case, moving carriage 111 will move the ultrasound probe 20 relative to the patient, and relative to the XY positioner 12, while the XY positioner 12 (and frame 114) stands fixed. Alternatively, the XY positioner may be fixed to carriage 111, e.g. through appropriate connecting means, such that the XY positioner moves integrally with carriage 111.

Figure 4:
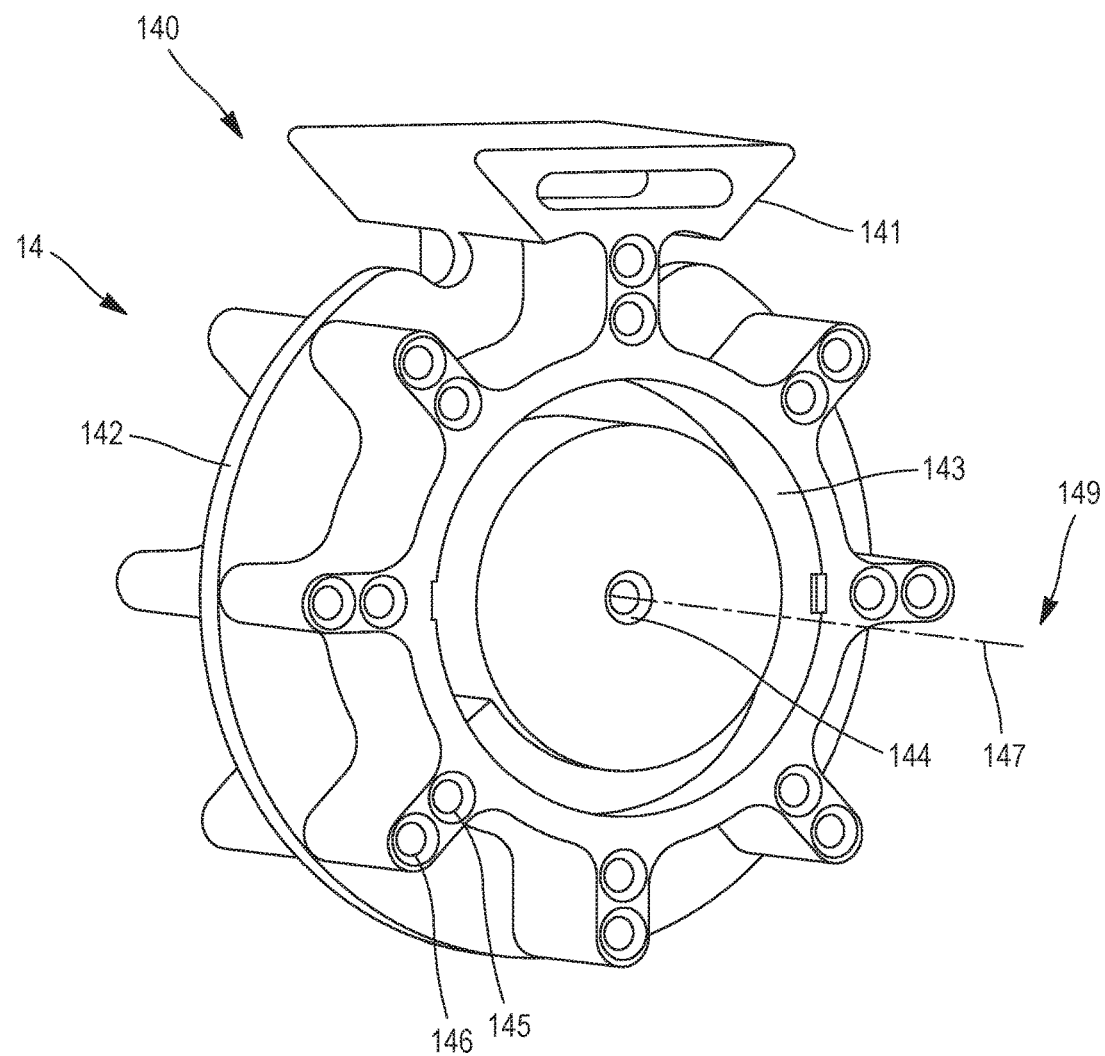
FIG. 4 represents a detailed perspective view of the guide for the electrode assembly as shown in FIG. 1.
Figure 5:
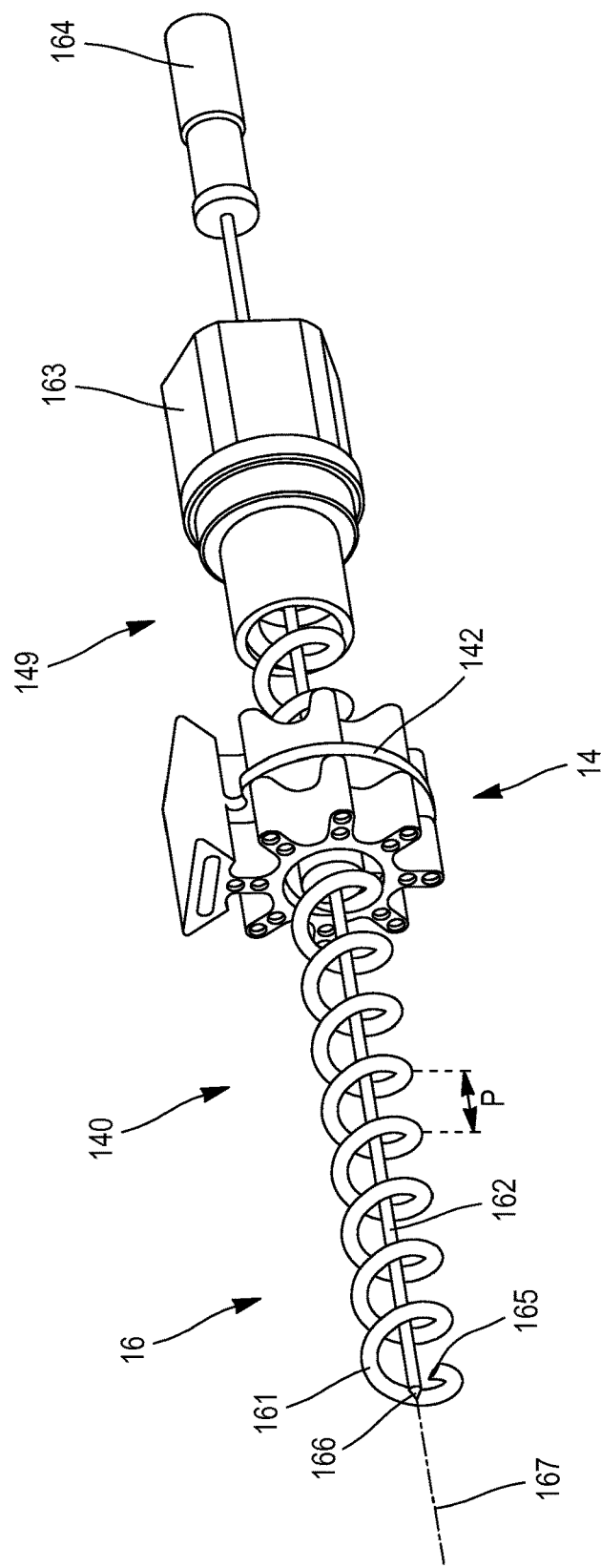
FIG. 5 represents a perspective view of the guide of FIG. 4 which holds a bipolar electrode assembly inserted through it.

Carriage 123 comprises a connector operable to fixedly hold a guide 14 for the electrode assembly. The connector may take the form of a dovetail clamp 125 operable to hold a corresponding dovetail connector 141 of the guide 14, as represented in FIG. 4. Connector 141 can be fixed in clamp 125 through set screw 126. The guide 14 further comprises a guide body 142 fixedly attached to connector 141, e.g. at a periphery thereof. The guide body 142 extends between a distal end 140 and a proximal end 149. A number of electrode insertion holes are provided through the body 142, and extend from the proximal end 149 to the distal end 140. A first one electrode insertion hole 143 is arranged for accepting and guiding a helical electrode 161 as represented in FIG. 5. Helical electrode 161 typically has a corkscrew like shape with advantageously constant pitch P and diameter. To this end, the insertion hole 143 may have a corkscrew like shape, with pitch and diameter corresponding to a pitch and a diameter of the helical electrode 161. It will be convenient to note that other shapes for the insertion hole 143 are possible without loss of functionality, e.g. the insertion hole 143 may have a sleeve-like shape with substantially cylindrical outer and inner walls extending throughout body 142 and provided with electrode retaining tags (not shown) at well-defined intervals within the insertion hole 143, such as intervals corresponding to a pitch of the helical electrode 161. Such electrode retaining tags allow the helical electrode 161 to be inserted through the insertion hole 143 by a corkscrew like movement and prevent linear motion of the helical electrode along an axis 147 of the insertion hole 143.

A second electrode insertion hole 144 may be arranged for accepting and guiding a straight needle electrode 162. The electrode insertion hole 144 is arranged through body 142 and concentric with the first electrode insertion hole 143. That is, electrode insertion holes 143 and 144 have coincident axes 147. When guide 14 is mounted to the XY positioner 12, the axes 147 of insertion holes 143 and 144 are advantageously parallel to the longitudinal axis 103.

Referring to FIG. 5, the electrodes 161 and 162 advantageously form a bipolar electrode pair and both extend along axis 167, between a tissue engaging tip 165 respectively 166 and corresponding handles 163, respectively 164. Sockets for connecting the electrodes to an external radio frequency generator 32 (FIG. 1) may be provided within handles 163 and 164.

It will be convenient to note that the straight needle electrode 162 may be replaced by a helical electrode (not shown) concentric to the outer helical electrode 161 and having a smaller diameter and advantageously a same pitch P as the outer helical electrode 161. Such a second helical electrode may be useful in particular when the outer helical electrode 161 would need to have a larger diameter. This allows to have a more uniform tissue ablation in the volume enclosed between the two helical electrodes. In such a case the insertion hole 144 would have a shape similar to electrode insertion hole 143. Alternatively, electrode assemblies having more than two electrodes may be used, such as a combination of two concentric helical electrodes having different diameters and a straight needle electrode concentric to the two helical ones, as described in WO 2009/138510 (FAURE) 19.11.2009 the contents of which are incorporated herein by reference. Such an electrode assembly may be operated by activating consecutively two out of the above three electrodes in a bipolar fashion.

The electrode guide body 142 may be provided with additional through holes 145, 146. These are advantageously provided externally of the first electrode insertion hole 143 (e.g., insertion hole for the largest helical electrode 161), and are advantageously arranged regularly around an outer circumference of the insertion hole 143 (through holes 145) and/or along a circumference of the guide body 142 (through holes 146). Through holes 145 may have axes arranged parallel to the axis 147 of the insertion hole 143 and be arranged at a constant distance of axis 147, e.g. radially, at regular angular intervals. Through holes 145, 146 are advantageously arranged in one (holes 145) or multiple orbits (holes 146) having different distance from axis 147 and arranged external to outer insertion hole 143. These through holes 145 and/or 146 may be used for inserting and guiding a straight needle electrode similar to electrode 162. When inserted through any one hole 145, 146, the straight needle electrode can be used in combination with helical electrode 161 to form a bipolar electrode pair for ablating an area or volume of tissue external to the helical electrode 161.

One problem observed with electrode positioning devices is tissue movement between the instant of positioning the electrode guide 14 and the instant when the tip 165 of the electrode 161 engages the tissue (organ) to be treated. Such tissue movement can be reduced by using prostate stabilisation needles (not shown) which prevent or reduce movement of the prostate gland while performing ablation or other intervention, such as a biopsy. Stabilisation needles have a specific design including deployable side barbs. The needle is inserted in the prostate and the side barb is deployed and its position locked, e.g. through a locking spring actuated at the proximal side, thereby achieving immobilisation of the prostate gland. Using a plurality of stabilisation needles (e.g., two) achieves improved immobilisation. Stabilisation needles can be obtained via SeeDOS Ltd, United Kingdom (Product No. 500118200) and Best Medical International Inc., VA, USA (Part #10207).

In order to allow effective use of the stabilisation needles, the assembly 10 according to aspects of the invention is provided with an additional linear motion guide 13 onto which is mounted a guide or template 15 adapted for insertion and guiding of stabilisation needles. To this end, linear motion guide 13 comprises a carriage 131 arranged for moving on guide 13 along axis 106. Advantageously, linear motion guide 13 is oriented parallel to linear motion guide 121 such that axes 104 and 106 are parallel. Advantageously, carriage 131 is configured to move along guide 13 independently of the movement of the XY positioner 12, e.g. independently of carriage 124 and/or carriage 123. FIGS. 2 and 3 represent views in which guide 13 and XY positioner 12 are arranged at different positions. By moving carriage 131 independently, a surgeon can easily position the needle template 15 at an optimal location for anchoring tissue, without regard to the location of the electrode assembly (guide 14).

Carriage 131 advantageously comprises a mount 132 onto which template 15 can be attached. Mount 132 can be fixedly secured to or be integral with carriage 131 and advantageously project in a direction perpendicular to axis 106, e.g. vertically. Template 15 can have any suitable shape, e.g. square, rectangular, triangular, pie shaped, etc. Advantageously, template 15 is attached on mount 132 through a pivot 133 having pivotal axis 134 advantageously orthogonal to axis 106, and advantageously parallel to the longitudinal axis 103. Pivot 133 advantageously allows for pivoting template 15 on axis 134, e.g. such that the template may be rotated on pivot 133 in a plane substantially parallel or tangential to the skin, and possibly for fixing template 15 at a desired angular orientation about axis 134 through appropriate means, e.g. a set screw.

Template 15 may be similar to templates used for brachytherapy. It may be shaped as a tab or plate provided with one or a plurality of through holes 151 for the insertion of stabilisation needles. Through holes 151 have axes 152 advantageously parallel to axis 147 of the guide 14 and/or axis 167 of the electrode assembly 16 when mounted, and advantageously parallel to the longitudinal axis 103.

Independent linear motion guide 13 and template 15 allow for positioning and inserting any stabilisation needles independently of the electrodes 161, 162. To this end, control knob 135, which is separate from the control knobs 127 and 128 of the XY positioner, allows for positioning carriage 131 along guide 13. This is particularly useful when the electrodes need to be retracted, repositioned and reinserted again in cases wherein their position is not in line with a treatment plan. If any hole 145 or 146 on the electrode guide 14 would be used for a stabilisation needle, this would have required retracting and reinserting the stabilisation needle to re-anchor tissue, as typically the electrode guide 14 would need repositioning for repositioning the electrodes.

Figure 7:
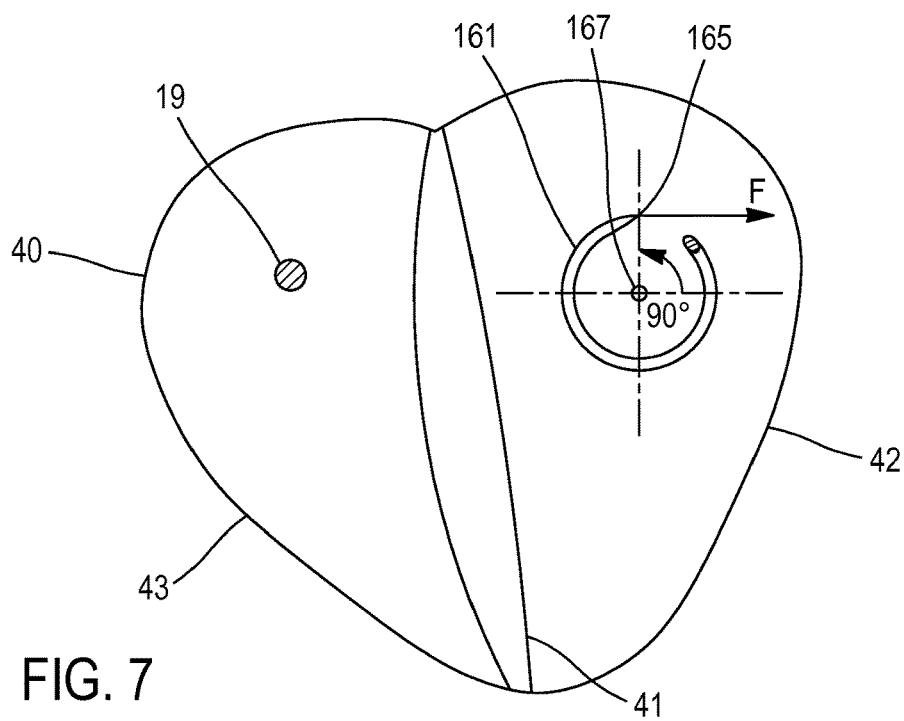
FIG. 7 represents a plan view of a prostate, a stabilisation needle anchored in a left part of the prostate and a helical electrode entering into engagement with the prostate in a right part thereof.

As shown in greater detail in FIG. 2, it may be advantageous to provide positioning means, such as in the form of an additional linear motion guide 17, for positioning the electrode guide 14 along longitudinal axis 103 and relative to the ultrasound probe 20. It has been observed that the orientation of tip 165 of the helical electrode 161 is critical at the onset of engaging the tissue or organ to be treated. Due to the curved nature of the helix, the tip imparts a force on the engaging tissue oriented tangential to the helix at the tip. By way of example, for a helical electrode having a right-handed helix as is the case for electrode 161 in FIG. 5, a helix tip 165 positioned at 180° (with 0° defined on a horizontal to the right of the axis 167 of the helix) will cause the engaging tissue to be moved upwards. Analogously, and referring to FIG. 7, a helix tip 165 positioned at 90° will cause the engaging tissue to be moved to the right. As a result, the area of the organ to treat may have shifted upon inserting the helical electrode. This is shown in FIG. 7 with regard to the prostate 40, which in plan view comprises a right part 42 and a left part 43 separated by the urethra 41. Generally, due to a lack of space, a stabilisation needle 19 is anchored to that part 43 of the prostate which is opposed to the area 42 of the prostate to be treated. If the helical electrode 161 is to engage the prostate 40 in the indicated orientation, i.e. with tip 165 at 90° relative to the helix axis 167, a force F imparted by the tip on the prostate will have an orientation indicated by the arrow on FIG. 7 and may cause the organ 40 to be deformed in a direction away from the anchor 19. As a result, the eventual position of the electrode 161 within the prostate may not satisfactorily correspond to a location of the tissue to be treated. Conversely, the situation depicted in FIG. 8, with electrode tip 165 engaging the prostate 40 under an angle of 270° provides improved stability as the engaging force is directed towards the anchored part of the organ 40.

Figure 8:
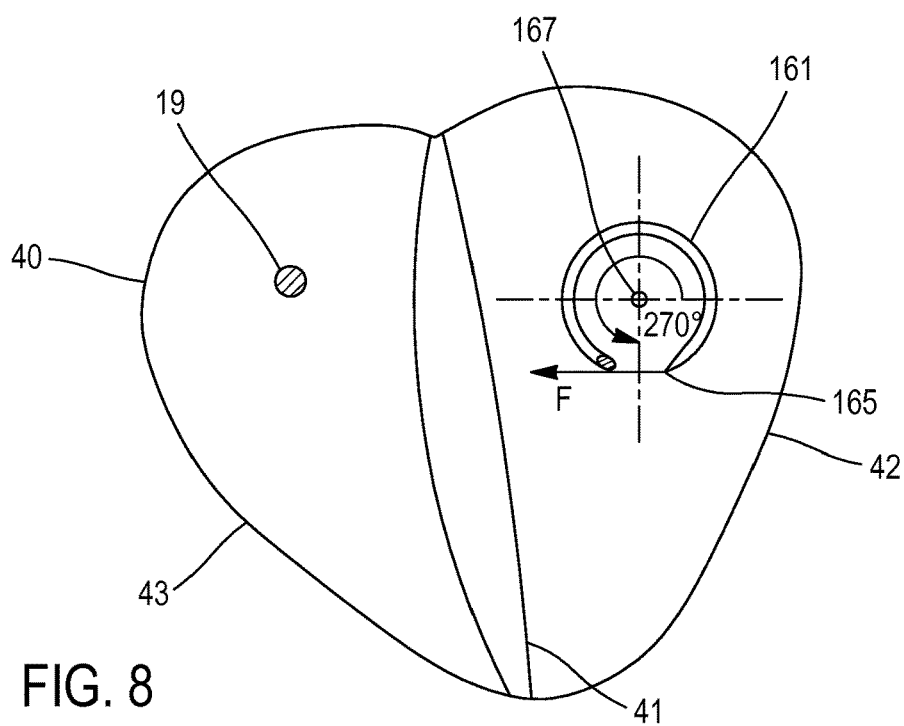
FIG. 8 represents the plan view of FIG. 7, with the helical electrode tip engaging the prostate from an opposite direction compared to FIG. 7.

The linear motion guide 17 allows for resolving the above undesired tissue movement by fine tuning the position of the electrode guide 14 along an axis 107 parallel to the longitudinal axis 103 for a fraction of the pitch of the helix of the electrode 161, e.g. repositioning the guide 14 over half the helix pitch will cause the helix tip 165 to engage the organ in the orientation of FIG. 8 instead of the orientation of FIG. 7. In general terms, it is advantageous to orient the helix tip so as to cause an engagement force directed towards the anchor or stabilisation needle.

Linear motion guide 17 can be mounted on assembly 10 in various ways. One possibility is to mount the linear motion guide 17 on carriage 123, such that it is aligned parallel to the longitudinal axis 103, which is shown in the FIGS. 1-3. Alternatively, the linear motion guide 17 can be mounted between the frame 114 and the XY positioner 12, such that the XY positioner 12 as a whole can move along motion guide 17, along longitudinal axis 103. Still other options, such as integrating linear motion guide 17 into XY positioner 12 to form a XYZ positioner are possible. It will be convenient to note that guide 17 can be operated independently of longitudinal guide 11, i.e. the guide 14 will be repositioned by guide 17 relative to the carriage 111 and ultrasound probe 20.

The linear motion guide 17 can either be operated manually, e.g. through control knob 171, or be connected to a treatment planning control and be provided with appropriate actuators for automatic control.

Figure 6:
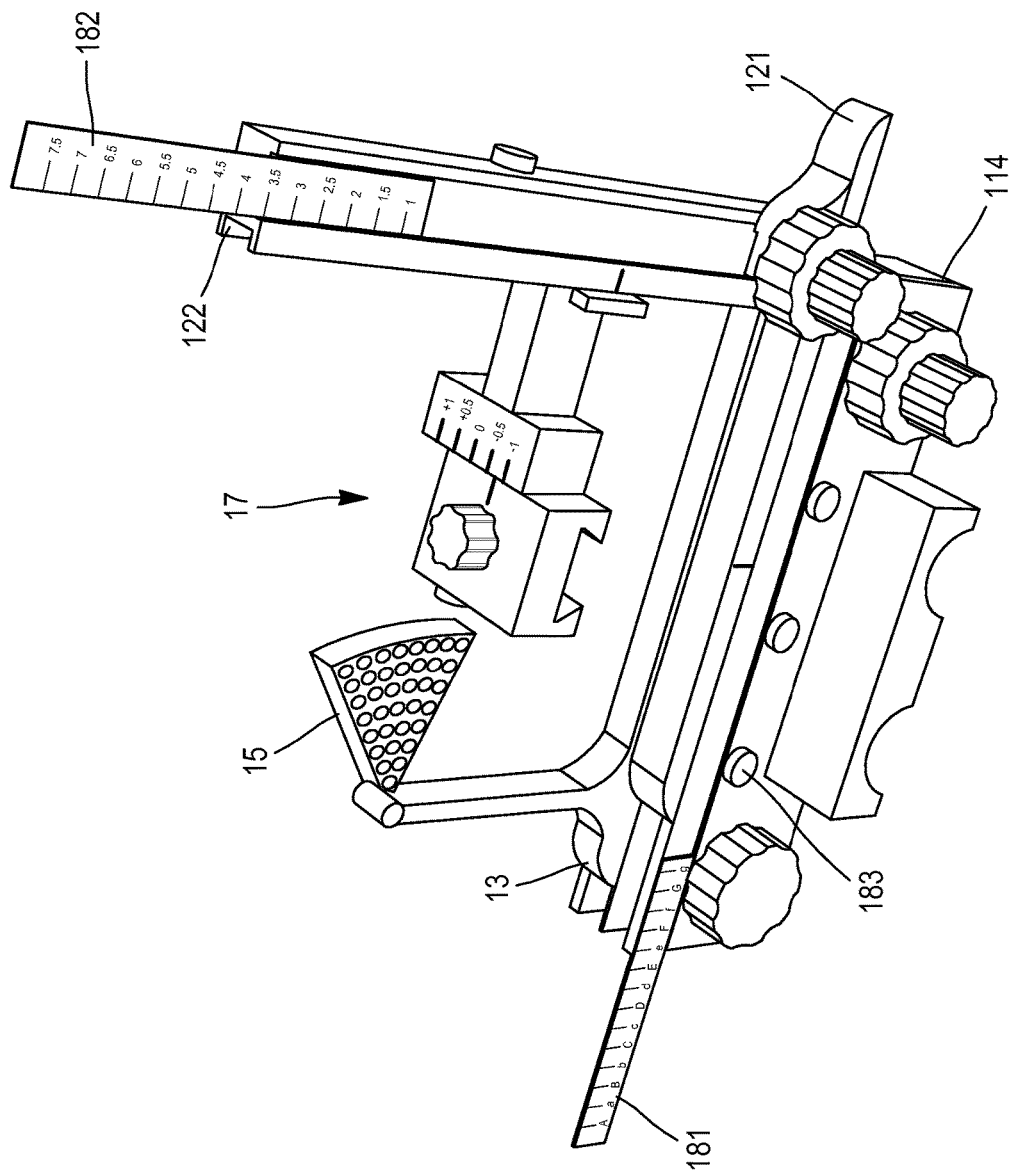
FIG. 6 represents a perspective view of the guide of FIG. 2 with repositionable rulers.

Referring to FIG. 6, any of the linear motion guides 11, 121, 122, 13 and 17 may be provided with a scale or position indication of the respective carriage relative to a reference. Advantageously, the position indication is provided on removable and/or repositionable rulers 181, 182. Rulers 181 and 182 can be moved along the corresponding guide 121, 122 respectively and positioned/fixed at a plurality of locations through set screw 183. By so doing, a reference position for the corresponding guide can be changed. Removable and/or repositionable rulers may be useful for the guides 121, 122 of the XY positioner, and additionally or alternatively for the longitudinal guide 17. In particular, rulers 181 and 182 may be positioned to provide correspondence with a coordinate system of the ultrasound probe 20. This may help the surgeon to easily read coordinates onto both the XY positioner 12 and the ultrasound image provided by probe 20. Alternatively, or in addition different sets of rulers can be mounted on assembly 10, depending on the type of ultrasound probe 20 used. In particular, different brands of ultrasound probes use different systems of position indication.

A calibration may be performed preoperatively in order to correctly position the rulers 181, 182 at a desired location. To this end, the assembly 10 with ultrasound probe 20 mounted on connector 112 is immersed in water and an ultrasound image from probe 20 is taken and displayed on a graphical user interface, such as a display screen 31. An operator then adjusts control knobs 127 and 128 to move carriage 123 of the XY positioner 12 to an origin of the coordinate system of the ultrasound image/probe. The correspondence can be monitored/verified by taking new ultrasound images with probe 20 and displaying on the screen. Rulers 181 and 182 may then be repositioned and fixed such that their reference corresponds to the position of carriage 123 and hence to the origin of the ultrasound probe coordinate system.

Assemblies 10 according to aspects of the present invention may be operated as follows. A treatment planning system 30 (FIG. 1) may determine beforehand an area of tissue, e.g. of the prostate, liver, pancreas, etc. to be ablated. Such systems are known. Preoperative planning may include selecting an appropriate electrode assembly 16 for radiofrequency ablation, in particular selecting a helical electrode 161 with a suitable diameter. The selected electrode assembly will determine the corresponding guide 14 that is to be used. This guide 14 is clamped in connector 125 of the carriage 123 of the XY positioner 12. The longitudinal linear motion guide 17 can be set at a zero reference position. An ultrasound imaging probe 20 is mounted in connector 112 on carriage 111.

Advantageously, the assembly 10 is now calibrated for correct position of the rulers 181 and 182, e.g. as indicated above. This allows to match the origin of a coordinate system of the ultrasound probe 20 with an origin or starting reference of the rulers 181 and 182.

The assembly 10 with ultrasound probe 20, possibly calibrated, is now installed in proximity of a patient to be treated. By way of example, a TRUS probe may be inserted through the rectum of the patient, e.g. by moving carriage 111 longitudinally along guide 11, to provide ultrasound images of the prostate, which is displayed on a display screen 31 of the treatment planning system. The treatment planning system 30 may now indicate a position for inserting the electrodes of the electrode assembly 16, e.g. a position for guide 14. The position for guide 14 may be a projected position, calculated by projecting an area of tissue to be ablated along an insertion direction of the electrode assembly in direction of the skin. One way for calculating the position of guide 14 is described in US 2011/0288541 the contents of which are incorporated herein by reference. In case the assembly 10 is completely manually operated, a surgeon or operator reads out on the display screen coordinates corresponding to the insertion position of the electrodes and moves the different linear motion guides of the system, in particular the guides of XY positioner 12, to position the electrode guide 14 in correspondence of the coordinates indicated by the treatment planning system. Alternatively, some or all the linear motion guides of the assembly 10 may be automatically driven by the treatment planning system 30. In such case, the treatment planning system 30 may send out instructions to actuators of the linear motion guides in order to move carriages, e.g. 111 or 123 of the assembly 10 to a calculated position under supervision of the surgeon.

Before inserting the electrodes 161 and 162 into the patient, the tissue, e.g. the prostate, is advantageously immobilised with the aid of stabilisation needles. Once guide 14 for inserting the electrode assembly is correctly positioned, e.g. as indicated by a treatment planning system, the surgeon may move carriage 131, e.g. by turning control knob 135, to a desired location in proximity of guide 14. Advantageously, template 15 may further be turned on pivot 133 in order to position a through hole 151 at a desired location for insertion of a stabilisation needle. A stabilisation needle is next inserted through through hole 151 and further through the patient's skin to arrive at the tissue to be treated, e.g. the prostate. An anchor is then deployed in the tissue through the stabilisation needle and the needle secured to the template 15 in order to provide improved stability during insertion of the electrodes. Additional stabilisation needles deploying further anchors may be used if desired.

Next, a bipolar electrode assembly is inserted through the holes 143 and 144 of guide 14. By way of example, the outer helical electrode 161 may be inserted first through hole 143 by turning it on longitudinal axis 103. Due to the shape of hole 143, turning the helical electrode 161 will result in moving the electrode 161 along longitudinal axis 103 towards the distal end 101. This allows inserting the helical electrode 161 through the skin and further to the tissue to be treated. Once the outer helical electrode 161 is correctly positioned, the inner electrode 162 may be inserted next, e.g. through hole 144. Alternatively, the inner electrode 162 may be inserted prior to inserting the outer helical electrode 161.

The electrodes are advantageously made of a material which is visible in the ultrasound images provided by probe 20, e.g. metal. This allows the surgeon to verify the insertion of either electrode through the tissue. Possibly, the treatment planning system 30 may be configured to monitor the insertion of the electrodes and compare their trajectory to a predetermined/projected trajectory.

In some cases, the actual trajectory of the electrodes deviates an unallowable amount, e.g. due to the organ or the patient having moved. In these latter cases, the electrode is removed from the patient. The electrode guide 14 may be repositioned for alignment to a new position of the tissue to be treated, before reinserting the electrode in the patient. Possibly, the treatment planning system 30 may be configured for recalculating a desired position of the electrode guide 14. It will be convenient to note that in cases wherein the electrode guide 14 needs to be repositioned, there is no need for repositioning template 15 and any stabilisation needle.

In some cases, the tip 165 of helical electrode 161 engages the organ comprising the tissue to be treated in an incorrect orientation, as discussed above in relation to FIGS. 7 and 8. A surgeon may note, e.g. on display screen 31, that the helical electrode tip 165 is engaging the organ from an undesired direction. In such case, the electrode may be removed from the patient and the guide 14 repositioned along longitudinal axis 103 by operating linear motion guide 17, e.g. by turning control knob 171. Advantageously, repositioning the guide 14 will not move the ultrasound probe 20, which remains at a fixed position. It will be convenient to note that the distance over which guide 14 needs to be repositioned along guide 17 will be less than one pitch of the helix of electrode 161.

Advantageously, the treatment planning system 30 is configured to calculate a distance between the guide 14 and a surface of the organ to be treated. The treatment planning system 30 can e.g. be implemented with logic to extract a position of the surface of the organ from ultrasound images taken by probe 20. Possibly, the assembly 10 may be provided with appropriate means, such as position sensors, allowing for communicating a position of guide 14 to the treatment planning system. Based on the calculated distance, the treatment planning system 30 can be configured to determine a position for the motion guide 17, allowing for the helical electrode 161 engaging the organ surface from a correct or desired direction.

The electrodes 161 and 162 are connected to an external radiofrequency generator 32, which may be provided within the treatment planning system 30, to form a bipolar electrode pair. Once the electrodes being correctly positioned, the radiofrequency generator 32 may be activated to supply radiofrequent energy to the electrodes, which heats the tissue enclosed by the helical electrode and eventually destroys it.

In some cases the area to be ablated is larger than an area enclosed by the outer helix 161. In such cases, following ablation of the area enclosed by helix 161, e.g. by electrode pair 161 and 162, a straight needle electrode such as electrode 162 can be inserted in one of the through holes 145 or 146 on guide 14 external to the helix 161. Such a configuration, with a straight needle electrode external to helical electrode 161, allows to ablate an additional volume of tissue interposed between the straight needle electrode and the helix, thereby increasing the area destroyed.

The invention claimed is:

1. An assembly for positioning an electrode assembly for radio-frequency ablation, comprising:
a first linear motion guide defining a first axis of motion, the first linear motion guide comprising a first carriage operable to move along the first axis of motion,
a connector adapted for attaching an imaging device to the first carriage, an XY positioner operable to move a second carriage in a two-dimensional space defined by a second axis of motion and a third axis orthogonal to the second axis of motion, wherein the XY positioner is positioned relative to the first linear motion guide such that the second axis of motion and the third axis are orthogonal to the first axis of motion,
a first coupling means for coupling the electrode assembly to the second carriage, characterised in that the assembly comprises:
a second linear motion guide defining a fourth axis of motion, wherein the second linear motion guide is disposed such that the fourth axis of motion is parallel to the second axis of motion, the second linear motion guide comprising a third carriage operable to move independently of the second carriage; and,
a second coupling means for coupling a tissue stabilising instrument to the third carriage;
wherein the first coupling means comprises a first instrument guide comprising a body having opposed surfaces and at least one first through hole extending between the opposed surfaces for guiding an electrode of the electrode assembly, the at least one first through hole defining a first guide axis.

2. The assembly of claim 1, wherein the first instrument guide and the second carriage comprise corresponding means for attachment.

3. The assembly of claim 1, wherein a first one of the at least one first through hole defines a helical pitch for insertion of a helical electrode of the bipolar electrode assembly, the helical electrode being of constant diameter and having a corresponding helical pitch.

4. The assembly of claim 3, wherein the first instrument guide comprises a second one of the first through holes being concentric to the first one of the first through holes.

5. The assembly of claim 1, wherein the first instrument guide comprises a third through hole arranged outside a cross-sectional circumference of the first one of the first through holes, the third through hole having an axis parallel to the first guide axis.

6. The assembly of claim 5, wherein the third through hole is straight and configured for passing a straight needle therethrough.

7. The assembly of claim 1, wherein the second coupling means comprises a second instrument guide comprising a body having opposed surfaces and second through holes extending between the opposed surfaces for guiding a tissue stabilising instrument, the second through holes defining a second guide axis, wherein the second instrument guide is mounted to the third carriage and the first instrument guide is mounted to the second carriage, such that the first guide axis and the second guide axis are parallel.

8. The assembly of claim 1, comprising a third linear motion guide defining a fifth axis of motion parallel to the first axis of motion, the third linear motion guide being operable to move the first coupling means along the fifth axis of motion.

9. The assembly of claim 8, wherein the third linear motion guide is mounted to the second carriage.

10. The assembly of claim 1, wherein at least one of a group consisting of the first linear motion guide, the XY positioner, the second linear motion guide and the third linear motion guide comprises a control knob for manual operation of a motion along the corresponding axis.

11. The assembly of claim 1, comprising a treatment planning system for operable connection to at least one of a group consisting of the first linear motion guide, the XY positioner, the second linear motion guide and the third linear motion guide for automatic operation of a motion along the corresponding axis.

12. The assembly of claim 1, comprising a ruler arranged for indicating a position of the second carriage along one of a group consisting of the second axis of motion, the third axis, and as the case may be, the fifth axis of motion, relative to a reference, and means for coupling the ruler to a corresponding one of the XY positioner and the third linear motion guide, wherein the means for coupling are adapted for fixing the ruler at different positions along the corresponding axis, the different positions representative of different ones of the reference.

13. An assembly for positioning an electrode assembly for radio-frequency ablation, comprising:

a first linear motion guide defining a first axis of motion, the first linear motion guide comprising a first carriage operable to move along the first axis of motion, a connector adapted for attaching an imaging device to the first carriage, an XY positioner operable to move a second carriage in a two-dimensional space defined by a second axis of motion and a third axis orthogonal to the second axis of motion, wherein the XY positioner is positioned relative to the first linear motion guide such that the second axis of motion and the third axis are orthogonal to the first axis of motion, a first coupling means for coupling the electrode assembly to the second carriage, characterised in that the assembly comprises:

a second linear motion guide defining a fourth axis of motion, wherein the second linear motion guide is disposed such that the fourth axis of motion is parallel to the second axis of motion, the second linear motion guide comprising a third carriage operable to move independently of the second carriage;

a second coupling means for coupling a tissue stabilising instrument to the third carriage; and, a pivot for pivotally coupling the second instrument guide to the third carriage;

wherein the second coupling means comprises a second instrument guide comprising a body having opposed surfaces and second through holes extending between the opposed surfaces for guiding a tissue stabilising instrument, the second through holes defining a second guide axis; and, the pivot, when assembled, has a pivotal axis being parallel to the second guide axis.

* * * * *